Figure 1:
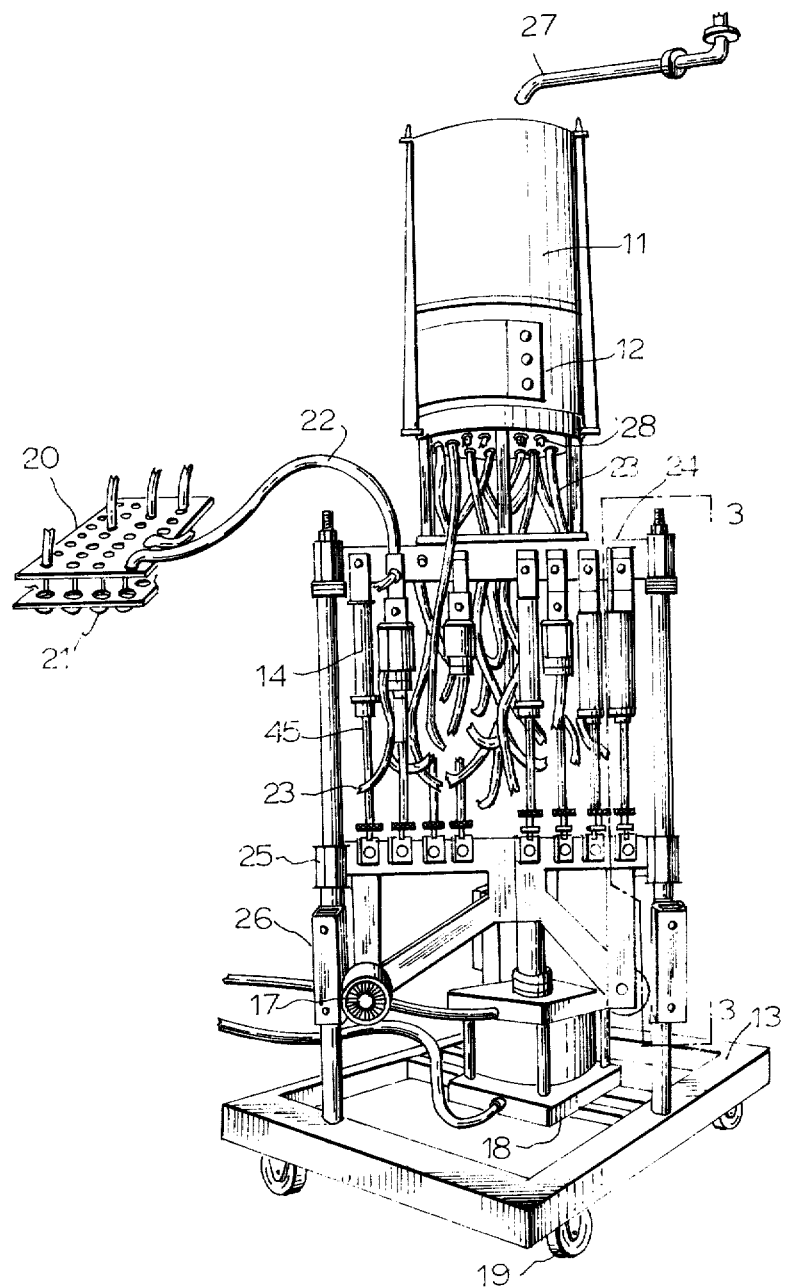

United States Patent [19]

Harrell et al.

[11] 3,939,883

[45] Feb. 24, 1976

[54] MACHINE TO FILL INSECT REARING CELLS WITH DIET

[75] Inventors: Edsel A. Harrell; Alton N. Sparks; William D. Perkins; Woodrow W. Hare, all of Tifton, Ga.

[73] Assignee: The United States of America as represented by the Secretary of Agriculture, Washington, D.C.

[22] Filed: Oct. 1, 1974

[21] Appl. No.: 510,974

[52] U.S. Cl. ............ 141/231; 141/238; 222/146 H; 222/255; 417/271
[51] Int. Cl.² .......................................... B65B 3/04
[58] Field of Search ............ 141/82, 100, 231, 232, 141/234, 237, 238, 240, 242, 243, 244; 222/146 H, 255; 417/271

[56] References Cited
UNITED STATES PATENTS

| | | | |
|---|---|---|---|
| 2,611,523 | 9/1952 | Aines | 141/231 |
| 3,031,106 | 4/1962 | Hooker | 222/146 H |
| 3,498,342 | 3/1970 | Sanderson | 141/238 |

Primary Examiner—Richard E. Aegerter
Assistant Examiner—Frederick R. Schmidt
Attorney, Agent, or Firm—M. Howard Silverstein; Max D. Hensley

[57] ABSTRACT

A new apparatus for metering insect diet accurately and efficiently into individual insect rearing cells is disclosed. Insect diet is accurately metered into a set of plastic rearing cells which are preformed by a form-fill-seal machine. The insect diet is transferred from a thermally controlled reservoir through a pneumatic cylinder type metering device by means of a negative pressure on the intake and a positive pressure on the discharge. Thus very high viscosity diet materials can be utilized. The diet is discharged through a set of nozzles into individual plastic rearing cells. A ball type check valve is used on both the intake and discharge ends of the metering device, which can be incrementally calibrated by a threaded collar type mechanism. The whole apparatus is mounted to a stationary frame with a movable lower cross-head which imparts function to the metering devices. The number of metering devices can be varied and assembled in series and operated simultaneously with the number of rearing cells.

4 Claims, 3 Drawing Figures

MACHINE TO FILL INSECT REARING CELLS WITH DIET

This invention relates to equipment that meters insect diet (food) into insect rearing cells. More specifically, this equipment was developed for use on a form-fill-seal machine which utilizes high impact polystyrene to mold individual rearing cells.

In prior art the literature teaches that the majority of experimentors used hand techniques to fill individual cells with diet for insects. This placed a severe limitation on the number of insect cells which could be handled for any one program. Rapid advances in insect rearing technology and increasing demands for laboratory reared insects at the lowest possible cost created a need for mechanization. To our knowledge there is no commercial equipment available that might be used in place of the instant invention.

Heretofore existing automatic equipment available on the market is limited to individual cell diet fillers and low viscosity diet filling machines.

In the instant invention it was necessary to use production equipment such as the form-fill-seal machine in mechanizing the insect rearing.

Prior art also teaches that there are varying degrees of viscosities of insect diet which must be used in the rearing of different kinds and types of insects. Variation in viscosity of material can completely frustrate automatic devices. Variation in temperature of diet as required by different insects can also add to design criteria.

The main objective of this invention is to provide an apparatus and method to suitably produce filled insect cells with diet (food).

Another object of the present invention is to produce filled cells with diet on a multiple basis and in mass assembly.

A third object of the invention is to handle multiple cells for filling with diet which varies widely in viscosity.

A fourth object of this invention is to be able to meter accurately and efficiently diet into insect rearing cells.

A fifth object of this invention is to be able to accurately control and vary the amount of insect diet fed to each cell.

Figure 3:
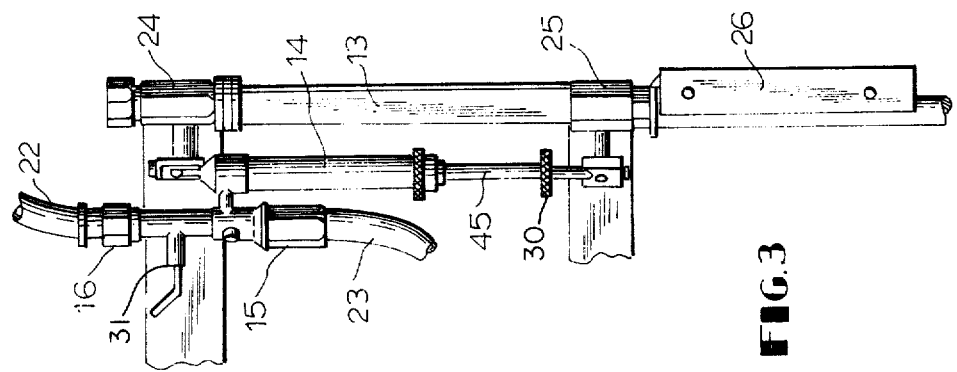
Figure 2:
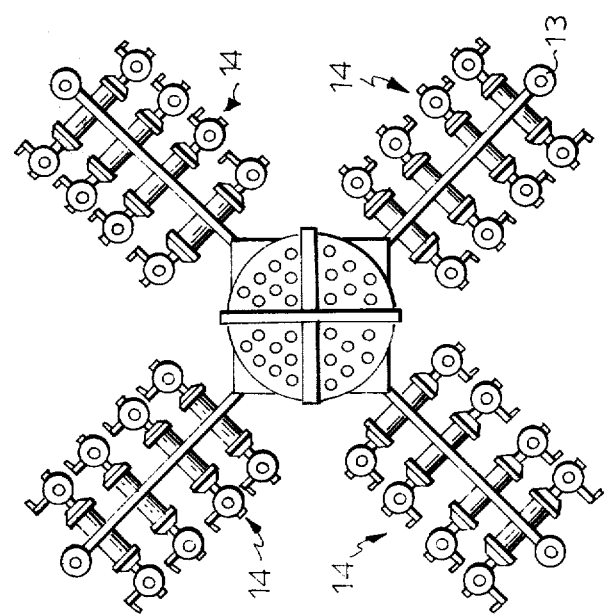

Other objects and advantages of this invention will further become apparent hereinafter and in the drawings, in which:

FIG. 1 is a pictorial view of the diet filler machine.
FIG. 2 is a top view of the diet filler machine.
FIG. 3 is a detail view of the filling cylinder and valves as attached to the frame.

In describing the preferred embodiment of the invention illustrated in the drawings, specific terminology will be resorted to for the sake of clarity. However, it is not intended to be limited to the specific terms so selected, and it is to be understood that each specific term includes all technical equivalents which operate in a similar manner to accomplish a similar purpose.

Turning now to the specific embodiment of the invention selected for illustration in the drawings, the equipment was developed for use on a form-fill-seal machine which utilizes high impact polystyrene to mold individual rearing cells at a variable speed measured in strokes. The form-fill-seal machine portion is not shown in the illustrative drawings. The number of cells can be varied and the number of strokes can be varied. For purposes of this demonstration, 32 individual rearing cells per stroke at a variable speed of up to 17 strokes per minute were chosen. The continuous plastic is formed in a web of cells and advanced horizontally 11 inches per stroke, then held motionless while the subsequent group of 32 cells are formed in a 4 × 8 cell pattern. Thus the insect diet filler was designed and synchronized with the operation of the form-seal machine to meter 5 ml of diet into each of 32 rearing cells per cycle. These cycles are continuous until the desired number of cells are fabricated and filled.

In operation insect diet comes to the filler reservoir 11 through pipe 27. It may come from a sterilizer or a pump (not shown in illustrative drawings). Reservoir shape and size is of importance only to support adequate capacity. Reservoir material is of major importance in that it must be compatible with resistance to deterioration by the insect diet composition. Reservoir 11 has adapters 28 in the bottom for attaching hoses 23. Insulation and electrical heater 12 are provided on the reservoir to keep the diet from cooling too rapidly. If the diet temperature is not too important the equipment may be used with or without the heaters. Most diets with high agar content should be heated. Agar content is the amount of material in the diet which is responsible for the gelling properties.

There is a metering cylinder 14 for each rearing cell to be filled. Since the insect diet is a viscous material it requires both negative and positive pressure to meter properly with this equipment. The negative pressure fills the metering unit and the positive pressure forces the diet from the metering unit through a hose and nozzle into the rearing cell. Each cylinder also has an inlet valve 15 which is a ball type intake check valve and an outlet valve 16 which is a ball type outlet check valve plus negative pressure hoses 23 and positive pressure hoses 22, as well as a safety valve 31 to regulate pressure. All cylinders are mounted to frame 13 which is set on casters 19. The instant invention was designed and built for 32 cylinders in this experiment. The top of the cylinders are held rigid since they are attached to stationary member 24, of the frame. Stem 45 which protrudes from the bottom of the cylinders is attached to a movable section 25 which is a bushing circumambient to a vertical post forming a vertical sliding means and is part of frame 13. Section 25 moves up and down and is powered by pneumatic cylinder 18. Braces and rollers 17 operating on stationary tracks 26 keep section 25 plumb, so that stem 45 in all 32 cylinders travels the same distance. When stem 45 is moved downward, a negative pressure is created inside cylinder 14. The negative pressure causes valve 16 to close and valve 15 to open, and this lets diet flow from the reservoir 11 through hoses 23 into each metering cylinder. Conversely, as stem 45 moves up, a positive pressure is created inside the metering cylinders. This positive pressure causes valve 15 to close and valve 16 to open, which lets diet flow from the cylinder through valve 16, hose 22, nozzles 20, and into the rearing cells 21.

The volume of diet is controlled by limiting the stroke of the driving cylinder. Therefore, the amount of diet placed in each cell is controlled by adjusting a collar on driving cylinder 18 to limit the stroke. Fine adjustments of less than two centimeters are made by using adjusting collar 30. Screwing the threaded collar in or out shortens or lengthens the stroke. Coarse adjustment of greater than two centimeters can be made by changing the collars.

Nozzles 20 are mounted in the same configuration of a 4 × 8 pattern and over the plastic web cell configuration. There is one nozzle per cell unit. The stroke of the metering cylinder 14 is adjusted to deliver between five and ten mls of insect diet to each of the 32 cells. The metering cylinder 14 is synchronized to deliver the diet to the cells during the period of time that the web is stationary in the form-fill-seal machine, and filling can be accomplished in less than two seconds. Metering cylinders 14 which are attached to movable part 25 are thus simultaneously driven by pneumatic cylinder 18, which is preset at the proper stroke.

The equipment is designed to deliver up to a maximum of 17 strokes per minute. However, empirical data indicate between 10 and 12 strokes per minute to be optimum. It should be coupled with a form-fill-seal machine that allows two second intervals for filling. Adequate space must be provided for the nozzles over the plastic cells.

Having described our invention, we claim:

1. An apparatus for filling insect rearing cells with diet comprising in combination:
  a. a means of storing insect diet, provided with a heater and insulated for temperature retention, said storing means attached to
  b. a plurality of vertical metering means wherein each vertical metering means comprises in combination:
    1. a vertical pneumatic cylinder having its upper end affixed to a upper horizontal stationary support for stability, and its lower stem end affixed to a lower horizontal movable support to impart function by upward and downward movement,
    2. an adjusting collar on said lower stem end for calibrating dispensed quantities of insect diet,
    3. a single passage serving for volume intake and outlet and communicating intermediate its ends with
    4. a working intake and outlet chamber in said cylinder
    5. a safety valve in said single passage to regulate pressure control
    6. an intake check valve at one end of said single passage operating within a negative pressure limitation and attached to
    7. a pressure hose supplying insect diet from said storing means under a negative intake pressure,
    8. an outlet check valve at the other end of said single passage operating within a positive pressure limitation and attached to
    9. a pressure hose dispensing insect diet under a positive outlet pressure,
  c. a frame comprising:
    1. a base mounted on casters,
    2. vertical post supports,
    3. said upper horizontal stationary support affixed to said vertical post supports at the ends thereof and also attached to the upper end of each vertical metering means,
    4. said lower horizontal movable support affixed to the vertical post supports by a vertical sliding means and also attached to the lower end of each vertical metering means thereby imparting controlled function by upward and downward movement to each metering means and said lower horizontal movable support attached to and actuated into upward and downward movement by a pneumatic means, said lower horizontal support also affixed to a system of braces and rollers which travel on vertical tracks affixed to the vertical post supports thus imparting stability and maintaining the vertical metering means plumb,
  d. a nozzle means communicating with said pressure dispensing hose for dispensing insect diet in controlled and preset quantity and into
  e. a rearing cell structure comprising individual cells.

2. The apparatus as defined in claim 1 wherein the adjusting collar is changeable to allow for both fine calibrations dispensing insect diet filler volumes of less than two centimeters and coarse calibrations dispensing insect diet volumes of greater than two centimeters.

3. The apparatus as defined in claim 1 wherein 32 metering means operate simultaneously arranged in 4 × 8 patterns.

4. The apparatus as defined in claim 1 wherein the materials of construction are of corrosion resistant materials.

* * * * *